United States Patent

Obermayer

Patent Number: 5,520,172
Date of Patent: May 28, 1996

[54] ANESTHETIC MACHINE

[76] Inventor: Anton Obermayer, Rudelsweiherstrasse 15A, 91054 Erlangen, Germany

[21] Appl. No.: 318,721
[22] PCT Filed: Apr. 16, 1993
[86] PCT No.: PCT/DE93/00348
  § 371 Date: Oct. 13, 1994
  § 102(e) Date: Oct. 13, 1994
[87] PCT Pub. No.: WO93/20875
  PCT Pub. Date: Oct. 28, 1993

[30] Foreign Application Priority Data

Apr. 16, 1992 [DE] Germany .............. 42 12 904.4

[51] Int. Cl.⁶ ............................................. A61M 16/00
[52] U.S. Cl. .................. 128/205.13; 128/203.28; 128/204.21; 128/205.18
[58] Field of Search .......... 128/203.12, 203.28, 128/204.21, 204.22, 204.23, 204.25, 204.26, 204.27, 204.28, 205.12, 205.13, 205.14, 205.15, 205.16, 205.17, 205.18, 205.19, 205.23, 910, 911, 912

[56] References Cited

U.S. PATENT DOCUMENTS

| | | | |
|---|---|---|---|
| 4,231,362 | 11/1980 | Pearson et al. | 128/205.15 |
| 4,453,543 | 6/1984 | Kohnke et al. | 128/203.28 |
| 4,538,605 | 9/1985 | Gedeon et al. | 128/205.24 |
| 4,909,246 | 3/1990 | Kiske et al. | 128/205.14 |
| 5,072,728 | 12/1991 | Pasternack | 128/204.18 |
| 5,119,810 | 6/1992 | Kiske et al. | 128/204.26 |

FOREIGN PATENT DOCUMENTS

| | | |
|---|---|---|
| 058706 | 9/1982 | European Pat. Off. . |
| 112979 | 7/1984 | European Pat. Off. . |
| 1904222 | 4/1970 | Germany . |
| 3712389 | 10/1988 | Germany . |
| 3820043 | 6/1989 | Germany . |
| 2062476 | 5/1981 | United Kingdom . |

Primary Examiner—Edgar S. Burr
Assistant Examiner—Eric P. Raciti
Attorney, Agent, or Firm—Spencer & Frank

[57] ABSTRACT

An anesthetic machine, in particular for use as ventilation part of an anesthetic system which has an inspiratory and an expiratory branch. In order to reuse, e.g. in a half-closed anesthetic system, part of the exhaled gas, the expiratory branch is connected via an additional line to the inspiratory branch. In addition, a controllable inspiration valve is used to control the respiratory gas removed from a gas store.

16 Claims, 9 Drawing Sheets

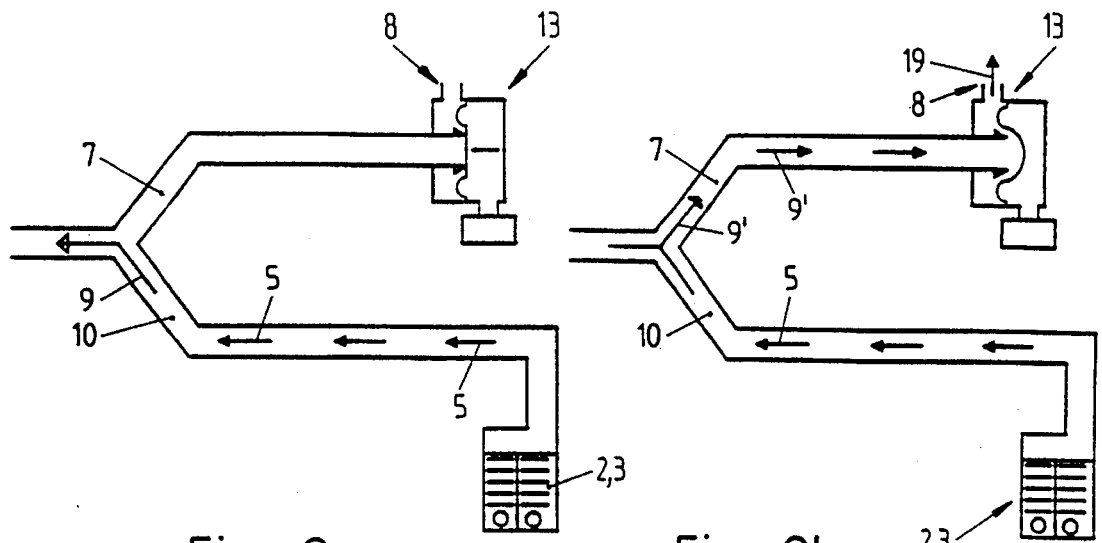
Fig 9a
PRIOR ART
Fig 9b
PRIOR ART
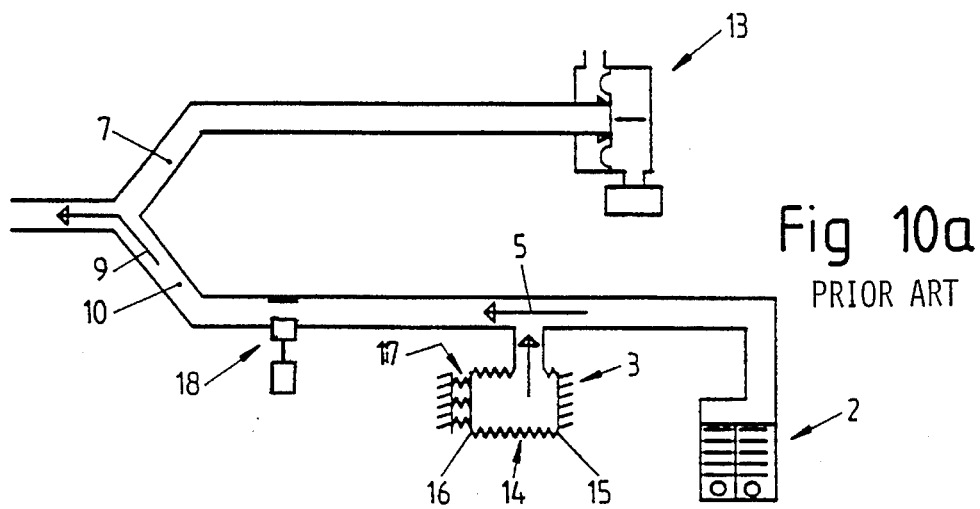
Fig 10a
PRIOR ART
Fig 10b
PRIOR ART

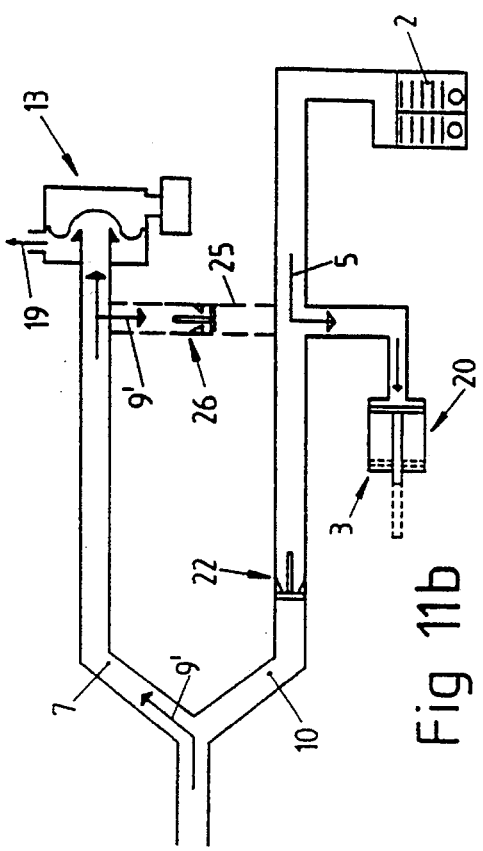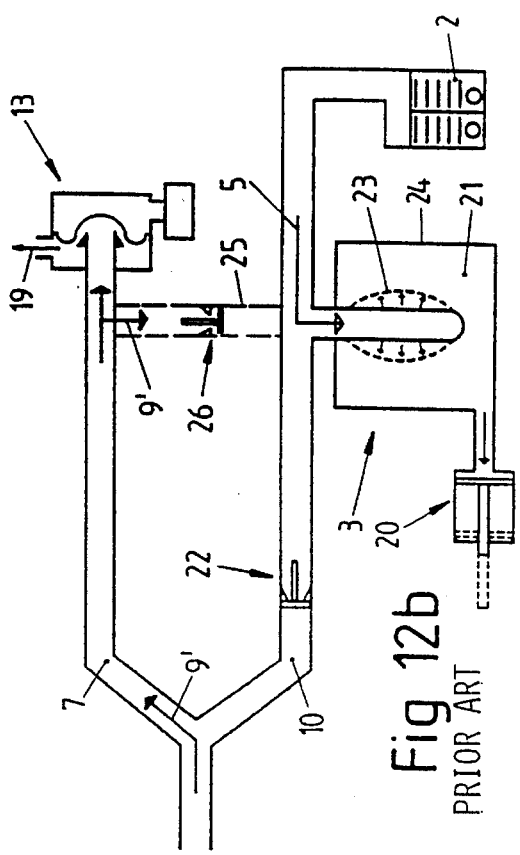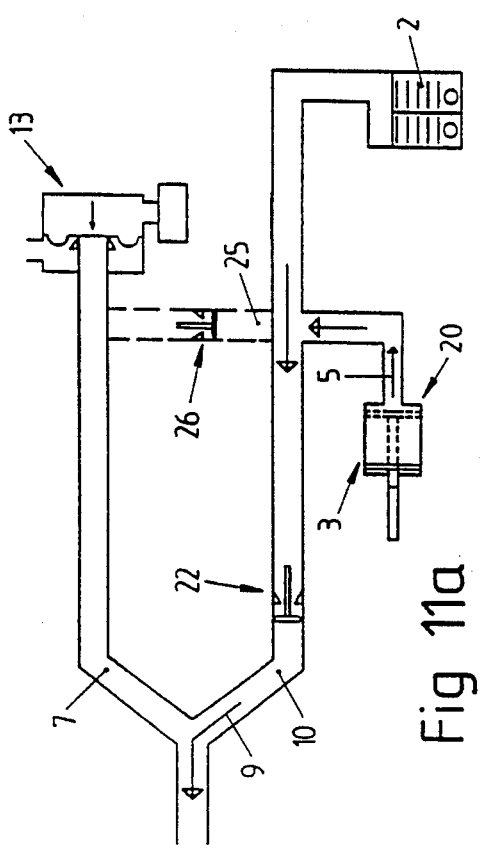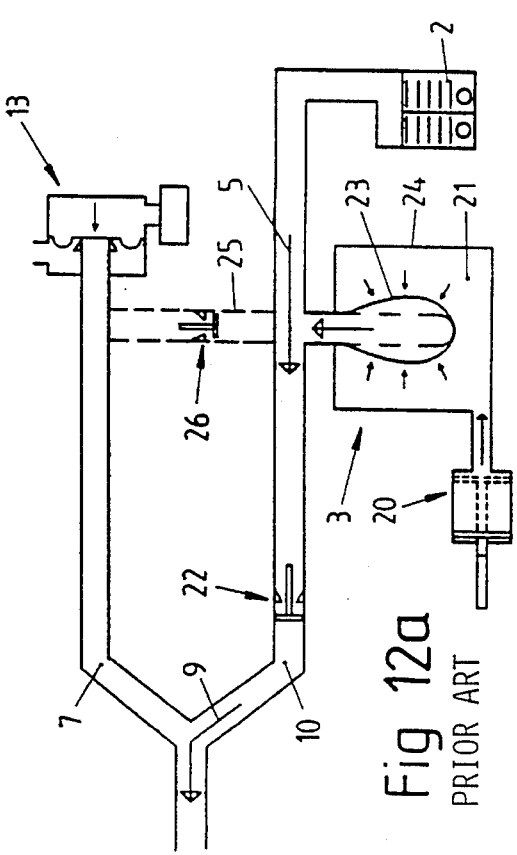

ANESTHETIC MACHINE

BACKGROUND OF THE INVENTION

The invention relates to an anesthetic machine.

A distinction is made in medical technology between anesthetic machines and ventilation systems.

Pure ventilation systems have been disclosed, for example, in the form of respiratory support machines as described, for example, in DE 38 20 043 A1, DE 37 12 389 A1 or EP 0 112 979 B1. Ventilation machines or respiratory support machines are used to ventilate patients before or after an operation in cases where the patient's own ability to breathe is insufficient.

By contrast, an anesthetic machine is used for the specific treatment of the patient during an operation. In the case of major surgical interventions, the anesthesia is, as a rule, carried out as so-called inhalation anesthesia. In this case, the patient is supplied by an anesthetic machine with the anesthetic gas mixture which is composed of oxygen, laughing gas and a vaporized anesthetic. At the same time, a ventilation is carried out. An anesthetic/ventilation machine is described, for example, in EP 0 058 706 B1.

The prior art relevant to the present invention is explained in detail in FIGS. 6 to 13 to improve understanding hereinafter.

Description of known anesthetic machines with various operating techniques:

As depicted in FIGS. 6 to 8, a known anesthetic machine 1 is essentially composed of three main groups, namely an anesthetic apparatus 2, a ventilation part 3 and an anesthetic system 4. The anesthetic apparatus 2 with a high-pressure gas supply is used to produce a fresh gas flow 5, i.e. an anesthetic gas mixture composed of oxygen, laughing gas and the anesthetic agent. The fresh gas 5 is passed continuously or intermittently into the anesthetic system 4.

The anesthetic system 4 represents the central functional unit of an anesthetic machine with which the actual gas exchange between the machine and the patient is brought about. Depending on the degree of unconsciousness, i.e. the depth of anesthesia, the gas exchange is achieved by the patient in the form of spontaneous breathing or, if spontaneous breathing ceases, by a mechanical or manual ventilation. In this case the ventilation takes place by the additional ventilation part 3.

The anesthetic systems 4 in use at present can be differentiated, depending on the reuse of the gas which is exhaled by the patient 6 and returned to the anesthetic system, into three different basic types which are depicted in FIGS. 6 to 8.

In the "half-open anesthetic system" depicted in FIG. 6, the gas which is exhaled and flows from the patient 6 back into the anesthetic system 4 through line 7 is not reused but completely removed from the system through the anesthetic gas extractor 8. The amount of gas (respiratory gas 9) required by the patient must be supplied to the anesthetic system 4 as fresh gas 5 from the anesthetic apparatus 2 via supply line 10. The gas supply line 10 is called the inspiratory branch and the gas removal line 7 is called the expiratory branch.

In the so-called "half-closed anesthetic system" depicted in FIG. 7, part of the exhaled gas is reused, i.e. the amount of gas (=tidal volume) supplied for inspiration by the patient consists partly of previously exhaled expiratory gas and only partly of fresh gas. A circulation 11 for this purpose is drawn as dotted line in FIG. 7, i.e. the expiratory gas from the expiration line 7 goes in one part to the anesthetic gas extractor 8 and in the other part (arrow 12) back to the inspiratory branch 10. This use of the expiratory gas makes it possible to achieve a considerable saving of fresh gas and simultaneously a conditioning of the inspiratory respiratory gas. The conditioning of the respiratory gas 9 in this case takes place by mixing the fresh gas 5 with the expiratory gas which has 100% humidity and a temperature of 37 degrees Celsius. The conditioning accordingly results in a warming and a moistening of the inspiratory respiratory gas. The smaller requirement for fresh gas 5 also makes an impact in terms of costs.

In the so-called "closed anesthetic system" depicted in FIG. 8, the expired respiratory gas 9' in the expiration line 7 is completely collected in the anesthetic system 4 and returned to the patient 6 at the next inspiration. This is depicted by the closed circulation 11 in FIG. 8, i.e. an anesthetic gas extractor is completely absent. The fresh gas flow 5 which is required is minimal in this system shown in FIG. 8 because it is necessary to supply only the oxygen used by the patient and the stored laughing gas and anesthetic agent. The fresh gas flow 5 is accordingly minimal, which also brings about low environmental pollution by the anesthetic gases due to absence of an anesthetic gas extractor. At the same time, optimal conditioning, i.e. warming and moistening, of the inspiratory respiratory gas 9 is achieved.

With all the anesthetic systems shown in FIGS. 6 to 8, artificial ventilation by the ventilation apparatus 3 is necessary, for example during an operation, because the patient's own respiratory system is switched off because of the anesthesia. In this case, the respiratory gas is supplied to the patient in the inspiratory phase with a slight increase in pressure of the order of 10 to 20 mbar. In the expiratory phase, an expiration valve is opened and the respiratory pressure is reduced to the ambient pressure (PEEP=0). In special cases an artificial increase in pressure in the expiratory phase may also be chosen, i.e. the expiration valve is set at a PEEP p>0, e.g. p (PEEP)≈2 to 5 mbar.

The anesthetic machines on the market are, as a rule, designed either only for the half-open anesthetic system or only for the half-closed anesthetic system or can be switched between the two systems.

For the ventilation part in the so-called "half-open anesthetic system", either so-called "flow choppers" or so-called "respirators with compressed gas store" are used. A "flow chopper" of this type with controlled expiration valve is depicted in FIGS. 9a and 9b. In this connection, FIG. 9a shows the inspiratory phase and FIG. 9b shows the expiratory phase. The reference numbers used in FIGS. 6 to 8 are also used further for the same parts hereinafter.

In the inspiratory phase shown in FIG. 9a, with the expiration valve 13 closed the patient's lung is filled by the fresh gas 5 which comes through the inspiratory branch 10 from the combined anesthetic apparatus 2 with ventilation machine 3 and high-pressure gas supply. In the expiratory phase shown in FIG. 9b, the patient is able to exhale through the expiration line 7 with the expiration valve 13 open. In this case, the continuous fresh gas flow 5 is, in the expiratory phase, likewise passed out through the expiration valve 13 to the outside or into an anesthetic extractor 8 (arrow 19). Recycling of the expired respiratory gas is not provided for. This system is therefore uneconomic and costly and requires an additional unit for conditioning the inspiratory gas.

There is no reuse of the expired gas from the patient's airway in the known half-open anesthetic system with a respirator with compressed gas store as depicted in FIGS. 10a, 10b. As depicted in FIG. 10a for the inspiratory phase, this anesthetic system has besides the anesthetic apparatus 2 an additional compressed gas store 14 as ventilation part 3 which consists of a fixed plate 15 and a movable plate 16 and of a pressure spring system 17. This half-open anesthetic system additionally has a controllable inspiration valve 18. In the inspiratory phase shown in FIG. 10a, the inspiration valve 18 is open and the controlled expiration valve 13 is closed. When the inspiration valve 18 is open, because of the pressure gradient between the compressed gas store 14 and the patient's lung, the fresh gas 5 flows through the inspiratory branch 10 to the patient. The compressed gas store 14 forming the ventilation machine is filled continuously or intermittently by the high-pressure gas supply of the anesthetic apparatus 2 until the pressure is about 5 bar. Very accurate gas metering is possible with the aid of the controllable inspiration valve 18 and also makes it possible to ventilate neonates. Besides good controllability, this system is distinguished by high gas tightness. However, the disadvantages are the high gas consumption and the lack of conditioning by the half-open anesthetic system because, in the expiratory phase depicted in FIG. 10b with the expiration valve 13 open, the expired respiratory gas is completely lost to the environment or in the anesthetic extractor 8 (arrow 19). During the expiratory phase, the inspiration valve 18 remains closed and the fresh gas 5 flows into the compressed gas store 14 and loads the latter up again against the force of the pressure spring system 17.

Another solution for a "half-open anesthetic system" according to the known system is indicated in FIGS. 11 and 12, with FIGS. 11a, 12a in each case depicting the inspiratory phases and FIGS. 11b, 12b depicting the expiratory phases.

In FIG. 11, a piston pump 20 is used as ventilation part 3 in place of the compressed gas store 14 in FIG. 10. This piston pump 20 is extended in FIG. 12 by the so-called "bag in the bottle" principle whose location is identified by reference number 21. In place of the controllable inspiration valve 18 in FIG. 10, a normal non-return valve 22 is provided in the exemplary embodiment shown in FIGS. 11 and 12.

In the exemplary embodiment shown in FIG. 11a, the piston pump 20 is actuated in the inspiratory phase and forces the fresh gas 5, which is present in the relevant cylinder space, through the automatically opening non-return valve 22 in the inspiration branch 10 to the patient. The controllable expiration valve 13 is closed in this phase. During the expiration phase shown in FIG. 11b, the expiration gas 9' exhaled by the patient flows into the expiration branch 7 and reaches the environment through the opened expiration valve 13 (arrow 19). The inspiration valve 22 in the inspiration branch 10 is closed during this phase. Because the inspiration valve 22 is designed only as non-return valve, the required ventilation pressure can in principle be built up only during the actual inspiration process, whose level depends on the elasticity of the patient's lungs and the flow resistance. However, it is also possible, by retracting the piston inside the piston pump 20, to convey, even during the expiration phase shown in FIG. 11b, part of the fresh gas 5 from the anesthetic apparatus 2 with high-pressure gas supply into the piston pump 20. However, the pressure which is built up in this inspiratory branch must be less than the expiratory pressure in the expiration branch 7 so that the non-return valve 22 remains closed.

The half-open anesthetic system shown in FIGS. 12a, 12b operates in principle in the same manner as described for FIGS. 11a, 11b. In this case, the fresh gas 5 is on each occasion removed or charged from the bellow or bag 23 of the unit 21. The gas flowing out of the piston pump 20 is moreover called the "primary system" inside the container 24, and the gas flowing out of the bag 23 is called the "secondary system".

However, the known system shown in FIGS. 11, 12 with piston pump 20 has considerable disadvantages in practice. The amounts of inspiratory gas required are between 5 ml and 2500 ml depending on the type of patient (infant or baby with a body weight below 2 kg or adult). Moreover, the piston advance of the piston pump 20 is not proportional to the amount of gas conveyed thereby and reaching the patient because, on the one hand, the gas is compressed and, on the other hand, there is further additional supply of fresh gas from the anesthetic apparatus 2. "Loading up" of the system is not possible because of the non-return valve 22 so that the inspiratory branch is subject to virtually no control. Furthermore, there is likewise a high consumption of fresh gas on the basis of the half-open anesthetic system shown in FIGS. 11, 12, associated with a lack of conditioning similar to the embodiment shown in FIGS. 9 and 10.

The known systems shown in FIGS. 11 and 12 can also be designed as so-called "half-closed anesthetic systems". In this case, the connecting line 25, which is drawn in the form of a broken line in FIGS. 11 and 12, is provided between the lower inspiratory branch 10 and the upper expiratory branch 7. An additional non-return valve 26 in the connecting line 25 is closed during the inspiratory phase shown in FIGS. 11a, 12a and open during the expiratory phase 11b, 12b. The expiratory respiratory gas 9' is accordingly able to reach the inspiratory branch 10 via the line 25 from the expiration branch 7 during the expiration phase. This is indicated with the appropriate arrows in FIGS. 11b, 12b. The abovementioned disadvantages with the restriction of an excessive consumption of fresh gas remain even in a half-closed anesthetic system of this type.

Finally, FIGS. 13a, 13b depict a known "half-closed anesthetic system" as has been further developed from the example shown in FIGS. 11a, 11b. In this case, FIG. 13a shows the inspiratory phase and FIG. 13b shows the expiratory phase of the anesthetic system. The difference from the exemplary embodiment shown in FIG. 11 is in the exemplary embodiment shown in FIG. 13 the provision in the expiratory branch of a controllable expiration valve 13 and, additionally, a controllable outlet valve 27. This valve arrangement makes it possible to determine the extent of the expiratory gas to be reused by means of the controllable outlet valve 27. If the outlet valve 27 is completely closed, the anesthetic system changes its function to a "closed anesthetic system" shown in FIG. 8, i.e. the complete expiratory gas 9' reaches the connecting line 25 to the inspiratory branch 10. The extent of the diversion of the expiratory gas is determined according to the degree of opening of the outlet valve 27. Accordingly, in intermediate positions, the anesthetic system is a so-called half-closed one as depicted in principle in FIG. 7. The arrangement depicted in FIGS. 13a, 13b accordingly has control advantages compared with the arrangement shown in FIGS. 11a, 11b. However, the mode of functioning in principle is the same.

The above description of the prior art shows the use in principle of anesthetic systems in the half-open, half-closed or closed modes of operation in each case. In general, this multiplicity of known anesthetic systems generally has the disadvantage that precise control of the inspiratory gas is impossible because even with a controllable inspiration valve 18 according to the known solution shown in FIG. 10, accurate metering and conditioning of the inspiratory gas is impossible. It is true that the fresh gas can be as it were "previously tensioned" by the compressed gas store 14 during the expiratory phase. However, circulation of the expiratory respiratory gas is not provided for in this known system.

SUMMARY OF THE INVENTION

The invention is based on the object of improving the known systems in such a way as to produce an anesthetic machine for all the modes of operation depicted in FIGS. 6 to 8, in which the minimum amount of fresh gas is required and optimal conditioning of the inspiratory gas is achieved.

This object is achieved starting from an anesthetic machine having ventilation means for supporting and performing ventilation of the patient. The ventilation means comprises a pressure generator comprising an alternating pressure gas storage device, and controllable actuation means for increasing the stroke volume of the gas storage device. The anesthetic machine further includes an anesthetic gas exchange means for performing a gas exchange between the anesthetic machine and a patient. The anesthetic gas exchange means includes an inspiratory branch supplying an inspiratory gas to the patient. The inspiratory branch has a first end attached to the pressure generator. An expiratory branch receives an expiratory gas from the patient. A patient connecting T-piece connects a second end of the inspiratory branch to a first end of the expiratory branch. A controllable inspiration valve is located in the inspiratory branch downstream of the pressure generator. The controllable inspiration valve includes means for removing a gas under pressure during an inspiratory phase from the gas storage device. An expiration valve is located in the expiratory branch. A connecting line connects the inspiratory branch to a location on the expiratory branch downstream of the expiratory valve to form one of a half-closed, closed, and half-open anesthetic system. The connecting line receives the expiratory gas from the patient and supplies the expiratory gas to the gas storage device. A controllable surplus valve is in communication with the expiratory branch. The controllable surplus valve includes means for controlling an amount of expiratory gas supplied to the gas storage device through the expiratory branch and the connecting line. The anesthetic machine further includes an anesthetic delivery means connected to the inspiratory branch for delivering fresh gas to the patient.

Advantageous and expedient further developments of the anesthetic machine as claimed in claim 1 are indicated in the dependent claims.

ADVANTAGES OF THE INVENTION

The invention is based on the central concept of combining the advantages of the known, previously described systems and producing, in particular, a controllable system in which one of the basic principles described in FIGS. 6 to 8 of the anesthetic systems employed is used as required. In this connection, as a general rule, the so-called half-closed anesthetic system shown in FIG. 7 will be used, with FIG. 6 and FIG. 8 in each case representing extreme cases. Accordingly, part of the respiratory gas expired by the patient is always returned to the inspiratory branch in order to use a minimum amount of fresh gas from the anesthetic apparatus, with the required amount of fresh gas being determined by the application and requirement of the patient. It is necessary for this purpose according to the invention for the inspiratory gas to be controlled by means of a controlled inspiration valve and likewise in the same way for the extent of the circulating airway gas to be controlled by a correspondingly controlled outlet valve. The anesthetic machine according to the invention with the components anesthetic apparatus, anesthetic system and ventilation system is therefore assigned a control system which controls the wide variety of functions of the individual elements and, in particular, the inspiration valve and the surplus valve or outlet valve and thus brings about the optimal conditions. It is moreover essential for the invention to provide an alternating pressure gas store which influences with a high pressure level the inspiratory phase. It is possible in this way to carry out the control of the inspiratory gas via the inspiration valve in a very sensitive and accurate manner, it being possible to use fresh gas and/or reusable expiratory gas from the alternating pressure gas store.

It is moreover important for the invention that the expiratory and reused gas is able simply to reach the alternating pressure gas store during the expiration phase. This is determined on the one hand by the setting of the controllable outlet valve and on the other hand by the reduced pressure in the alternating pressure gas store itself.

"Alternating pressure" for the purpose of the invention means that the pressure in the gas store can be reduced to zero or slightly below zero to receive the expired gas and/or the fresh gas and, for carrying out the ventilation, can be compressed to a defined working pressure before the start of the inspiration phase.

Besides the accurate metering of the inspiratory gas flow and, associated therewith, also of the inspiratory gas volume, considerable problems always arise with conventional anesthetic machines in the half-closed anesthetic system when it is necessary, with newer anesthetic and therapeutic methods, for the patient to breathe spontaneously from the anesthetic machine for a lengthy period. The technical difficulties associated with this type of application are that the anesthetic machine must suit the gas flow to the patient to the patient's spontaneous breathing behavior. In particularly difficult situations it is moreover necessary to supply the patient not only with the amount of gas necessary for spontaneous breathing but also to provide—for very weak patients—additional respiratory support or spontaneous breathing assistance. In the system according to the invention this is achieved by supplying the gas via the controllable inspiration valve by a measurement of the reduced pressure and/or gas flow generated by the patient when breathing spontaneously. The measuring unit for the reduced pressure and/or gas flow generated by the spontaneously breathing patient is called the trigger unit.

BRIEF DESCRIPTION OF THE DRAWINGS

Further details and advantages of the invention are explained in the following description of exemplary embodiments which are described in detail by means of the depictions in the figures.

FIGS. 9a and 9b illustrate the inspiratory and expiratory phases, respectively, of a known anesthetic machine.

FIGS. 10a–12b illustrate a known half-open anesthetic system.

DETAILED DESCRIPTION

Figure 1A:
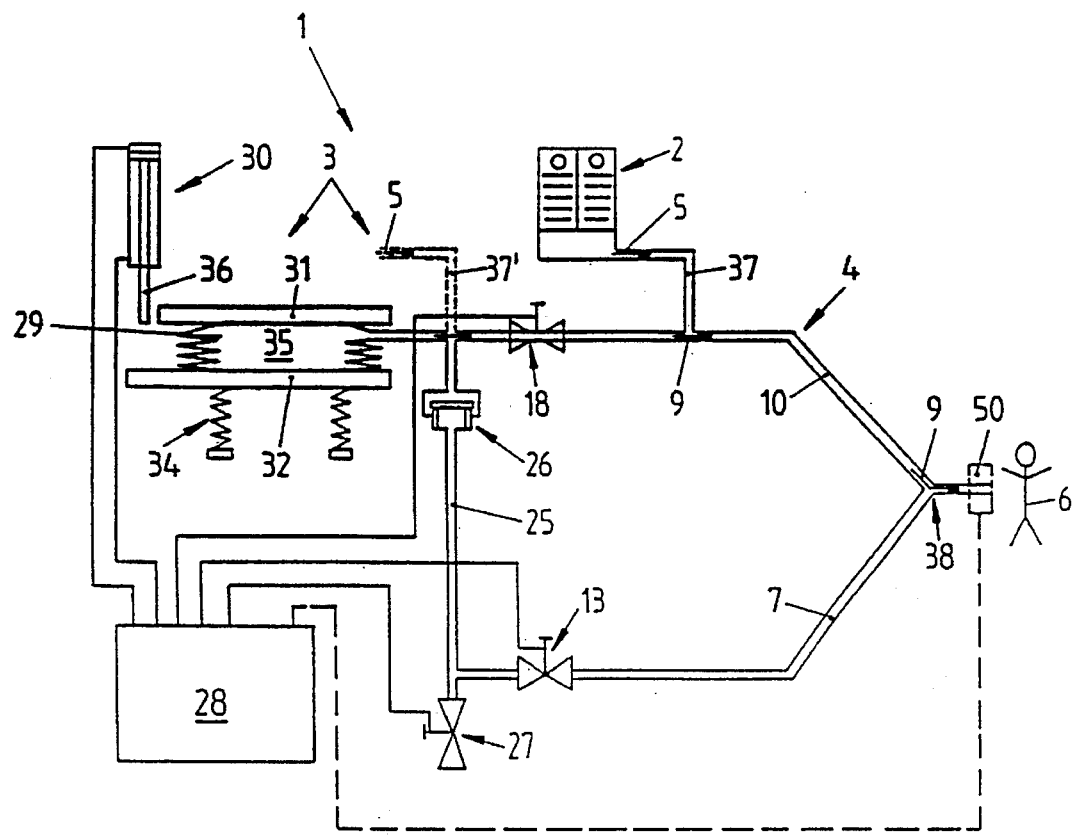
FIGS. 1*a*, 1*b* show a standard system for a half-open, half-closed and closed anesthetic system.

In FIGS. 1 to 5, identical parts are labeled with identical reference numbers as long as they have already been used for identical parts in the description of the prior art shown in FIGS. 6 to 13.

In general, the problem is solved for all the exemplary embodiments shown in FIGS. 1 to 5 by a connecting line 25 with non-return valve 26 (i.e., check valve) always being present between inspiratory branch 10 and expiratory branch 7 and permitting return of the expiratory respiratory gas 9' to the inspiratory branch 10. A controllable inspiration valve 18 and a controllable outlet valve 27 are present for the inspiratory phase and are connected to a control unit 28. In addition, a pressure generator 29, which is designed as an alternating pressure gas store, is provided as ventilation part 3 and can be moved by a separate or integrated pneumatic or electrical piston cylinder unit 30. It is possible by means of the piston cylinder unit 30 to reduce the pressure in the alternating pressure gas store 29 in order to permit problem-free uptake of the expiratory gas during the expiration phase.

The alternating pressure gas store 29 can be designed as any type of unit for maintaining pressure constant. In the exemplary embodiments shown in FIGS. 1 to 5, this gas store consists of a fixed plate 31 and of a movable plate 32 with a spring bellows 33 located between them. A spring system 34 located underneath the movable plate 32 serve for automatic actuation of the gas store. It is also, of course, possible to use a positively driven piston cylinder unit to produce the gas space 35 inside the gas store 29.

The piston cylinder unit 30 has a pneumatically or electrically driven piston rod 36 which applies a force to the movable plate 32 during the expiratory phase so that the gas volume 35 is increased. In this case the piston rod 36 is in turn controlled via corresponding lines leading to the control unit 28.

The inspiration phase depicted in FIG. 1a operates as follows:

Shortly before the start of the actual inspiration phase the piston rod 36, which is shown here by way of example, is moved back into the initial position by the control unit 28, which releases the movable plate 32 of the alternating pressure gas store 29. The spring forces of the spring system 34 which now become effective compress the gas store and generate the working pressure necessary for inspiration. This working pressure is of the order of two to three times the usual ventilation pressure, i.e. e.g. about 60 mbar. The control system of the control unit 28 closes, via an appropriate control line, the expiration valve 13 for the actual inspiration by the patient 6 and, at the same time, opens the inspiration valve so that the desired inspiratory gas flow is produced between the gas store 29 and the patient 6. In this case, the patient's lung represents an elastic gas store into which the respiratory gas flows. This respiratory gas flowing into the lung increases the pulmonary pressure as a function of the tissue elasticity and the amount of gas flowing in. To maintain the inspiratory gas flow it is therefore necessary to adjust the inspiration valve 18 appropriately by the control unit 28.

After administration of the tidal volume necessary depending on the patient, the inspiration valve 18 is closed and the patient's lung is left in the inflated state for a short time. This is called the so-called inspiratory pause.

During the inspiration phase it is possible for the fresh gas, which has been taken from the anesthetic apparatus 2 with high-pressure gas supply, to be supplied separately via a separate line 37 to the inspiratory branch 10. It is moreover possible for continuous or intermittent supply of fresh gas 5 to take place via line 37.

Figure 1B:
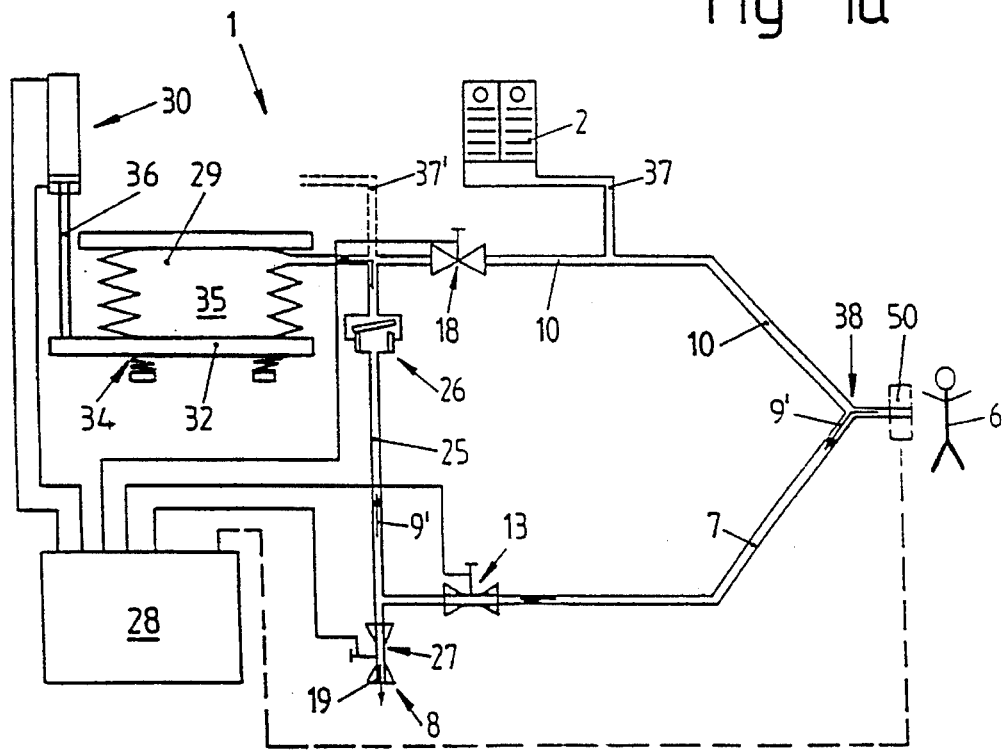

The supply line 37 for the fresh gas can, as depicted in FIGS. 1a, 1b be located between the inspiration valve 18 and the patient-connecting T piece 38. In this case, the supply of fresh gas is unaffected by the setting of the controllable inspiration valve 18 during the inspiration phase. The same applies to the expiration phase which is depicted in FIG. 1b and in which the supply of fresh gas is expediently operated intermittently. This operation is also controlled by the control unit 28.

As depicted in FIGS. 1a, 1b the fresh gas supply 37' for the fresh gas 5 can also be located between the alternating pressure gas store 29 and the inspiration valve 18 as depicted by a dotted line. In this case, the gas flow of the fresh gas supply is picked up by the control system of the inspiration valve 18 so that fresh gas can also reach the gas store 29 and thus the ventilation part 3.

The expiration phase depicted in FIG. 1b operates as follows:

Shortly before or at the same time as the switchover to the expiration phase, i.e. at the time when the expiration valve 13 opens, the piston rod 36 is moved out by the control system of unit 28 and thus the movable plate 32 is pushed downwards against the spring forces of the spring system 34. The increase in volume of the gas space 35 in the gas store 29 means that the pressure in this gas store falls to zero or, in some circumstances, even to a reduced pressure slightly below zero. After opening of the expiration valve 13, owing to the positive pressure in the lungs of the patient 6, the expiratory gas flows through the expiratory branch 7 and the connecting line 25 through the non-return valve 26, which is open in this case, into the gas store 29. During this phase there is also control of the outlet valve 27. Depending on the degree of opening of the outlet valve or surplus valve 27, the expiratory gas 9' is passed into the gas store 29 or out of the system (arrow 19). The amount of expiratory gas which is not required can accordingly be passed via the surplus valve into the anesthetic gas extractor 8 (arrow 19). This applies in particular as a function of the increasing pressure in the storage system.

Accordingly, the main advantage of the apparatus system according to the invention is the accurate control of the inspiratory gas flow. Moreover, the half-closed anesthetic system with an alternating pressure gas store 29 is preferably used, with the expiratory gas being supplied to the gas store partly or completely (closed anesthetic system) and only the unrequired amount exhaled being removed in the anesthetic gas extractor. In this case, control takes place via the gas pressure in the gas store 29 and the control of the outlet valve 27 which is downstream of the expiration valve 13. The inflow of expiratory gas to the gas store 29 can be solved without difficulty by the piston cylinder unit 30 according to the invention, it also being possible to use another driven gas cylinder unit 29.

It is, of course, also possible for the expiration valve 13 to be designed as so-called PEEP valve.

Figure 2A:
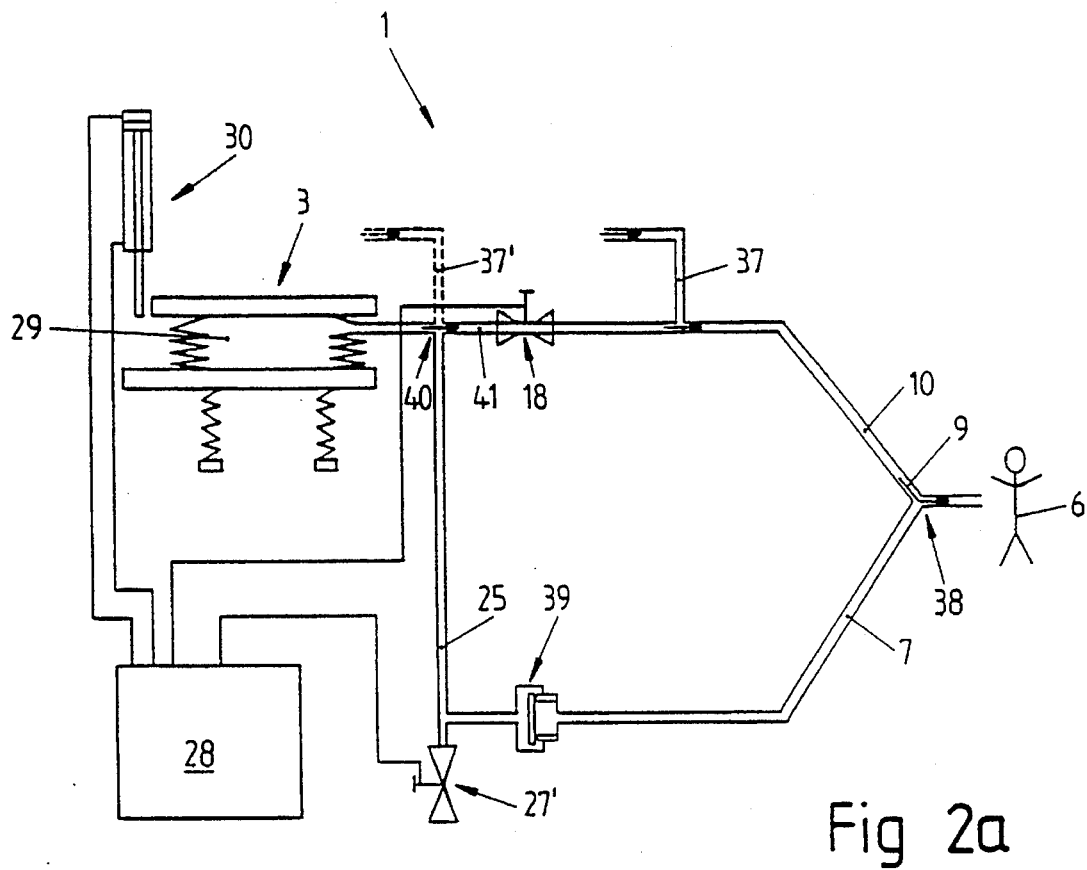
FIGS. 2*a*, 2*b* show a simple system for a half-closed anesthetic system.
Figure 2B:
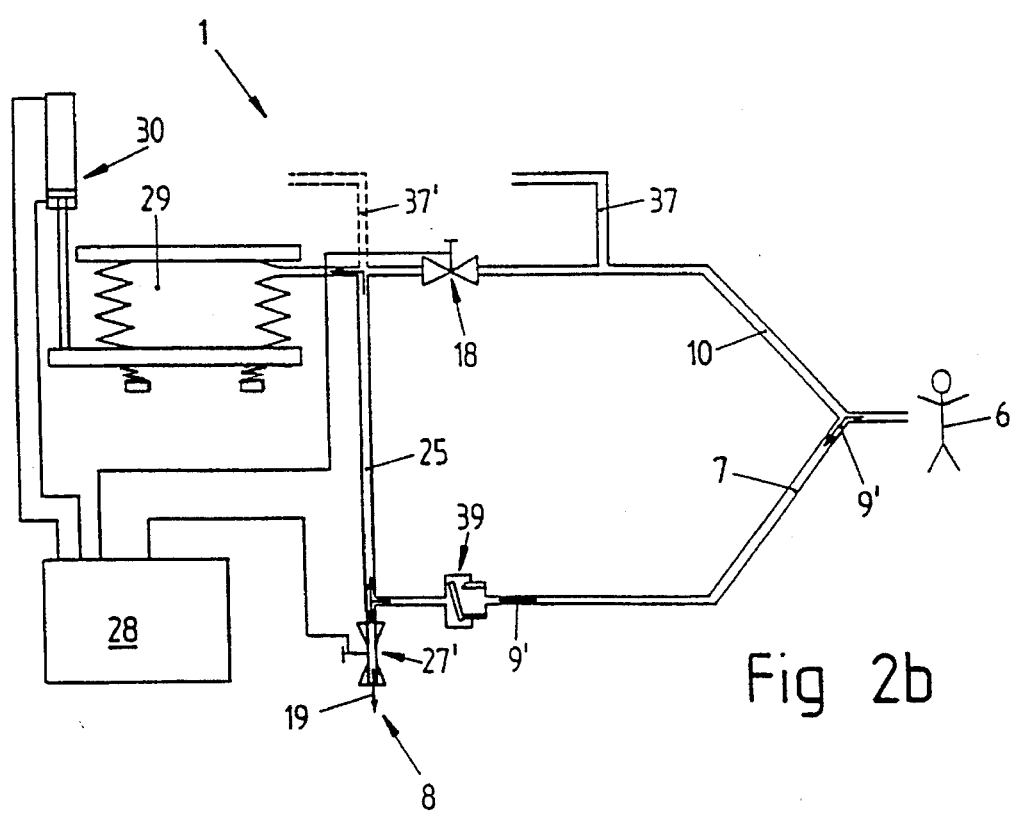

A simplified system for the half-closed anesthetic system is used in the exemplary embodiment of the invention shown in FIGS. 2a, 2b. In this case, identical parts are labeled with identical reference numbers as in FIGS. 1a, 1b.

In the simplified exemplary embodiment shown in FIGS. 2a, 2b, the non-return valve 26 in the line 25 is dispensed with because this connecting line 25 between the expiratory branch 7 and the inspiratory branch 10 can also be closed in other ways during the inspiratory phase shown in FIG. 2a. For this purpose the expiration valve 13 present in FIG. 1a is replaced by a simple one-way valve 39, while the outlet valve 27' is designed as combination valve, i.e. as combined surplus, expiration and/or PEEP valve. This makes it possible for the expiratory branch 7 and the surroundings or the anesthetic waste gas extractor to remain closed during the inspiratory phase shown in FIG. 2a.

During the expiratory phase shown in FIG. 2b, the one-way valve 39 opens so that the expiratory gas 9' can reach, depending on the setting of the combination valve 27', the gas store 29 likewise via the connecting line 25 or the anesthetic gas extractor 8 via the combination valve 27' (arrow 19). The functioning of this gas guidance takes place in the same way as described for FIGS. 1a, 1b.

Figure 3A:
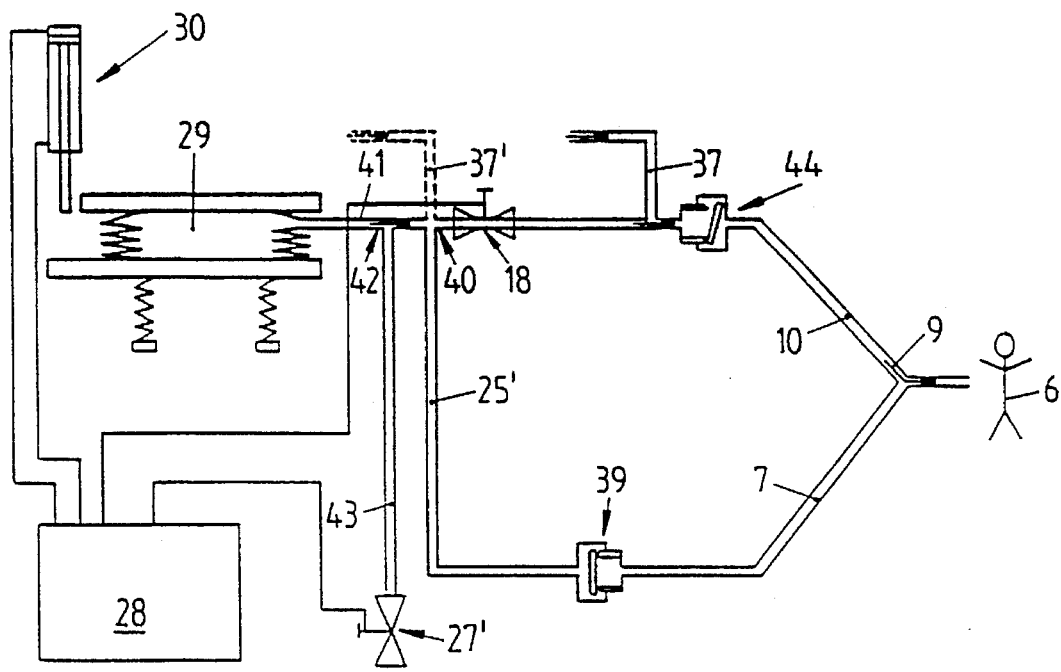
FIGS. 3*a*, 3*b* show an anesthetic breathing system in the case of existent circulation system types with integrated, exchangeable inspiration valve.
Figure 3B:
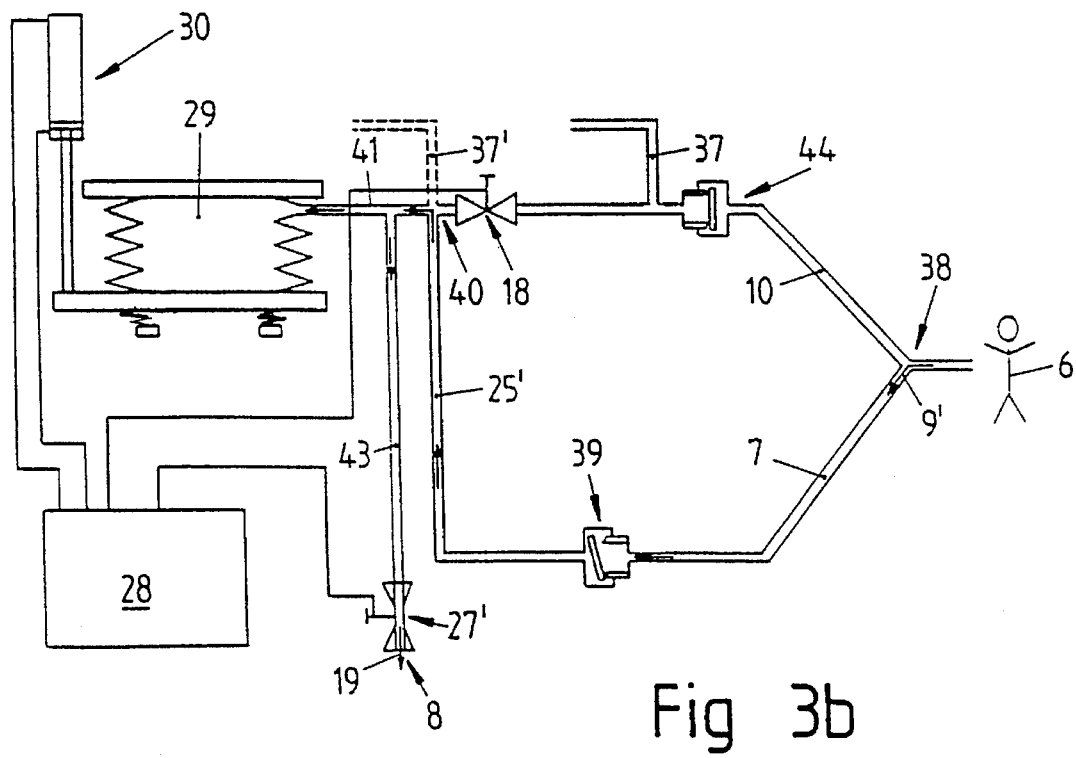

In the exemplary embodiment which is also present and is shown in FIGS. 3a, 3b, an anesthetic breathing system of the type shown in FIGS. 2a, 2b is provided, in which existent circulation system types with integrated, replaceable inspiration valve 18 are used. In this embodiment identical reference numbers again designate identical parts.

Figure 8:
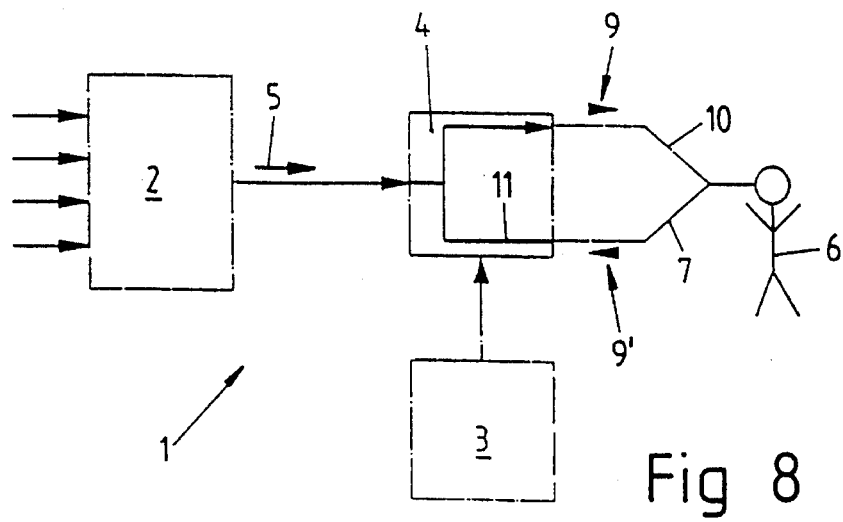
Figure 13A:
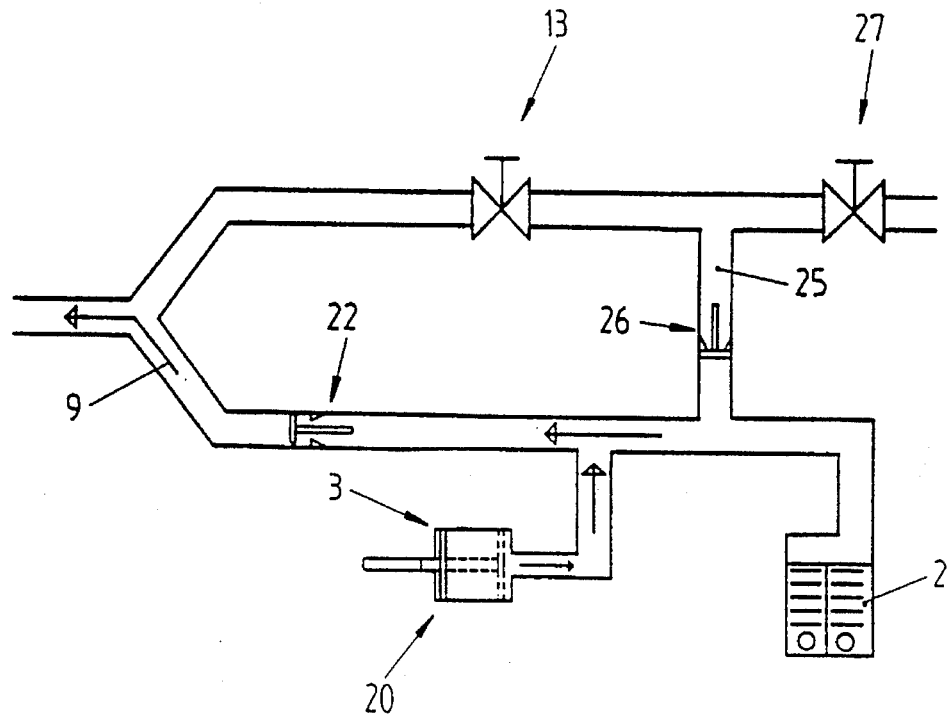
FIGS. 13a and 13b illustrate a known half-closed anesthetic system.
Figure 13B:
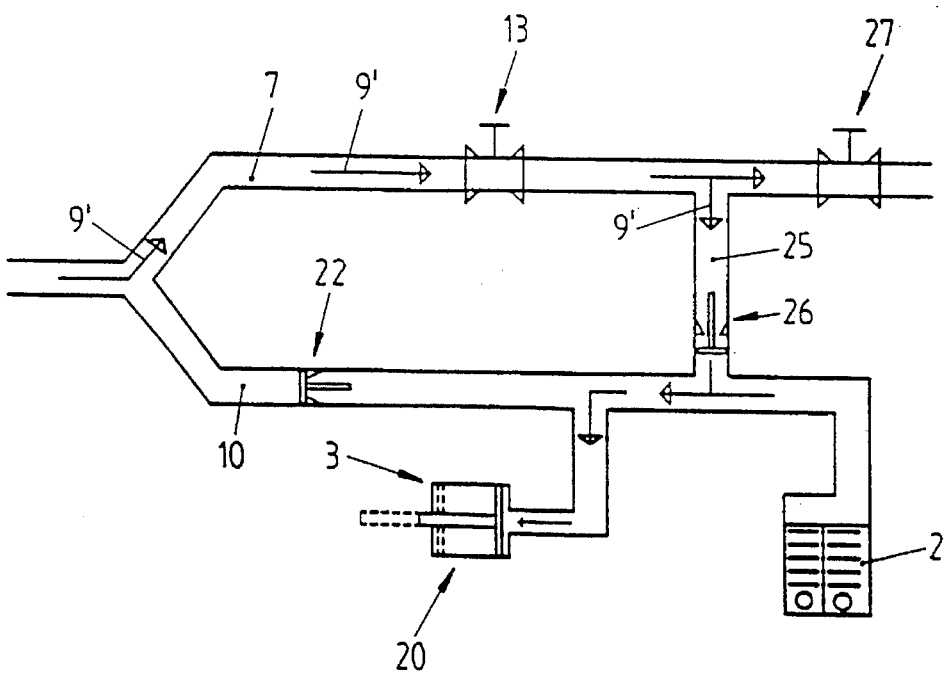

Compared with the exemplary embodiment shown in FIGS. 2a, 2b, in the case of the exemplary embodiment shown in FIGS. 3a, 3b a first gas return line 25' which forms a circular line as depicted in FIG. 8 for the closed anesthetic system is provided in the existent circulation system. The expiratory gas 9' is accordingly always returned through the one-way valve 39 into the inspiratory branch 10 and reaches, via a T piece 40, the inspiratory line 41 between gas store 29 and the controllable inspiration valve 18, as is also the case in the exemplary embodiment shown in FIGS. 1 and 2. In contrast to the two exemplary embodiments mentioned, however, the combination valve 27' is connected, not in the expiratory branch 7 but in the inspiratory branch 10, via another T piece 42 to the inspiratory line 41 between gas store 29 and inspiration valve 18, so that an additional gas line 43 for the expiratory branch results.

Accordingly, during the inspiratory phase, both the non-return valve 39 and the combination valve 27' are closed, so that the inspiratory gas reaches the patient 6 via the inspiratory branch 41, 10 from the gas store 29 and from the additional fresh gas supply 37 or 37'. This corresponds to the gas guidance according to the exemplary embodiment shown in FIG. 2a.

During the expiratory phase as depicted in FIG. 3b, the non-return valve 39 opens and the expiratory respiratory gas reaches the T piece 40 via the connecting line 25' and from there reaches the gas store 29 via the line 41. Depending on the position of the controllable combination valve 27' the expiratory surplus gas is diverted via the additional gas line 43 into the anesthetic gas extractor 8 (arrow 19). In this expiratory phase it is possible for the inspiration branch to be closed by an additional one-way valve 44. This one-way valve 44 is located between the patient-connecting T piece 38 and the inspiration valve 18. The fresh gas supply 37 of the anesthetic apparatus 2, which is not depicted in detail, is located between the one-way valve 44 and the inspiration valve 18.

Figure 4A:
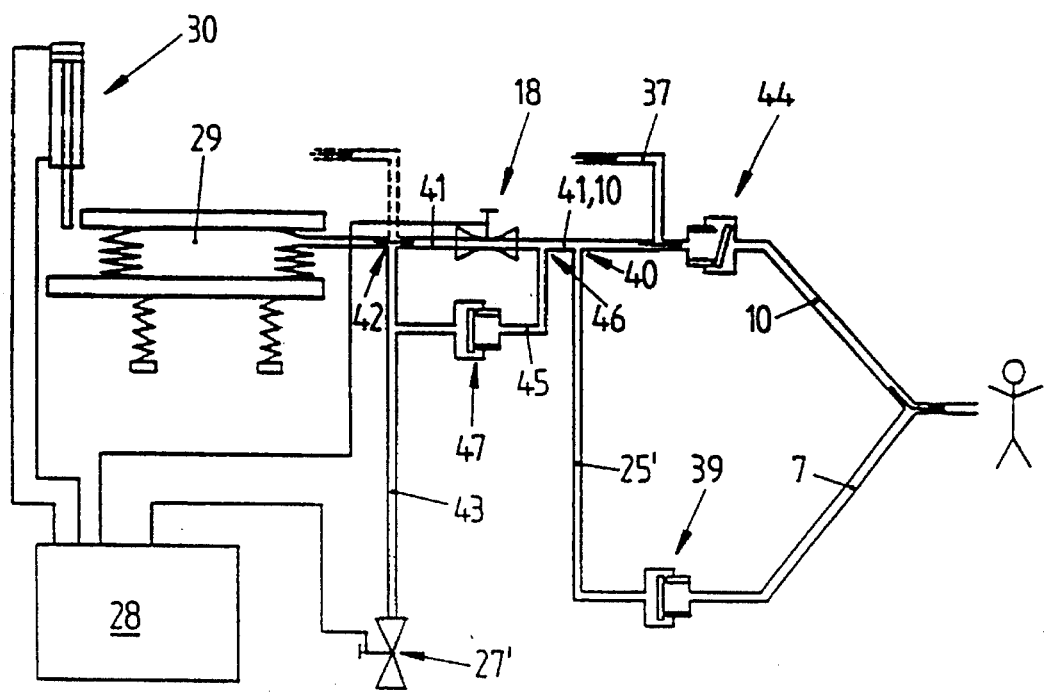
FIGS. 4*a*, 4*b* show a valve combination for connection of anesthetic breathing systems in the case of existent circulation system types
Figure 4B:
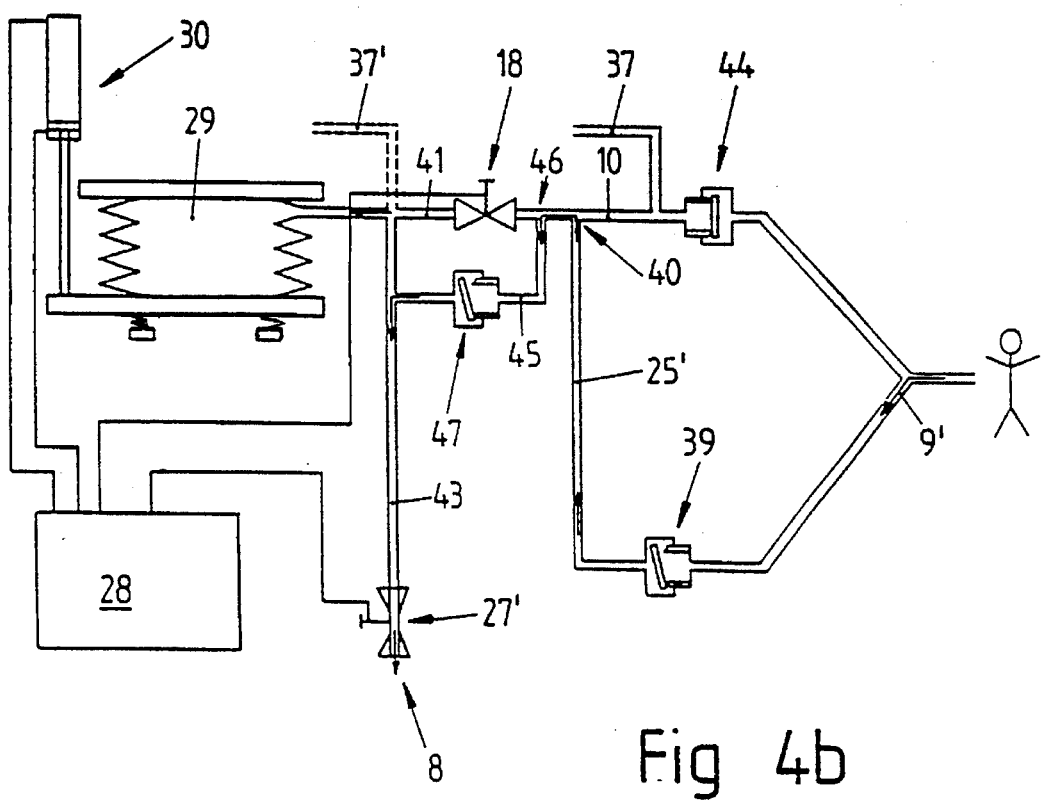

FIGS. 4a, 4b depicts another exemplary embodiment of the invention as a modification of the exemplary embodiment shown in FIGS. 3a, 3b. Identical parts are identified by identical reference numbers. This valve combination is used for connecting an anesthetic breathing system in the case of existent circulation system types.

In a further development or modification of the system shown in FIGS. 3a, 3b, the inspiration valve 18 is located outside the circulation system. According to the exemplary embodiment of the invention shown in FIGS. 4a, 4b, the expiratory gas is supplied, in a line 45 which is connected in parallel to line 41 and runs from the T piece 40 in the inspiratory branch 10 via another T piece 46, to the parallel line 45 in order to bypass the inspiration valve 18. Another one-way valve 47 is located in this parallel line 45 and is closed during the inspiratory phase shown in FIG. 4a and open during the expiratory phase shown in FIG. 4b. It is thus possible for the inspiratory gas to reach the patient during the inspiratory phase, when the one-way valve 47 is closed and the combination valve 27' is closed, only via the controllable inspiration valve 18.

During the expiration phase shown in FIG. 4b, the expiratory gas 9' reaches the inspiratory branch 10, via the one-way valve 39 and the return line 25, and from there reaches the additional gas line 43 via the connecting line 45, the one-way valve 47. Depending on the opening of the combination valve 27', the expiratory gas is in turn supplied to the gas store 29 or, via the combination valve 27', to the anesthetic gas extractor 8. It is possible where appropriate for the line 25' to be directly connected to the line 45.

Figure 5A:
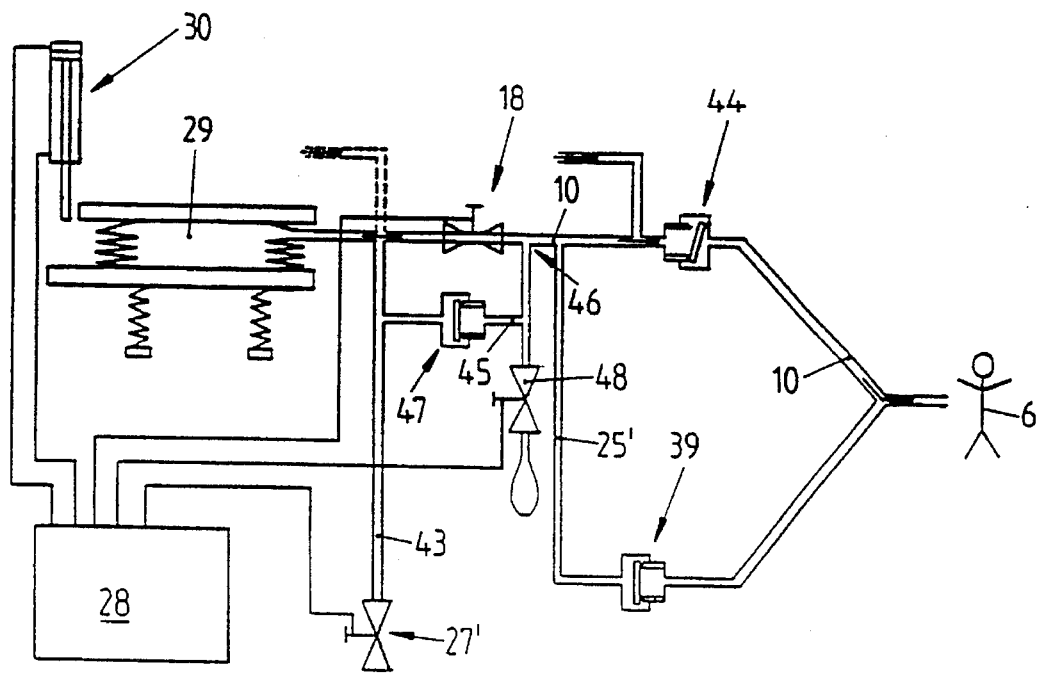
FIGS. 5*a*, 5*b* show a system after the variation of FIGS. 1 to 4 with connectable manual ventilation, where Figure a in each case shows the inspiratory, and Figure b shows the expiratory, ventilation process.
Figure 5B:
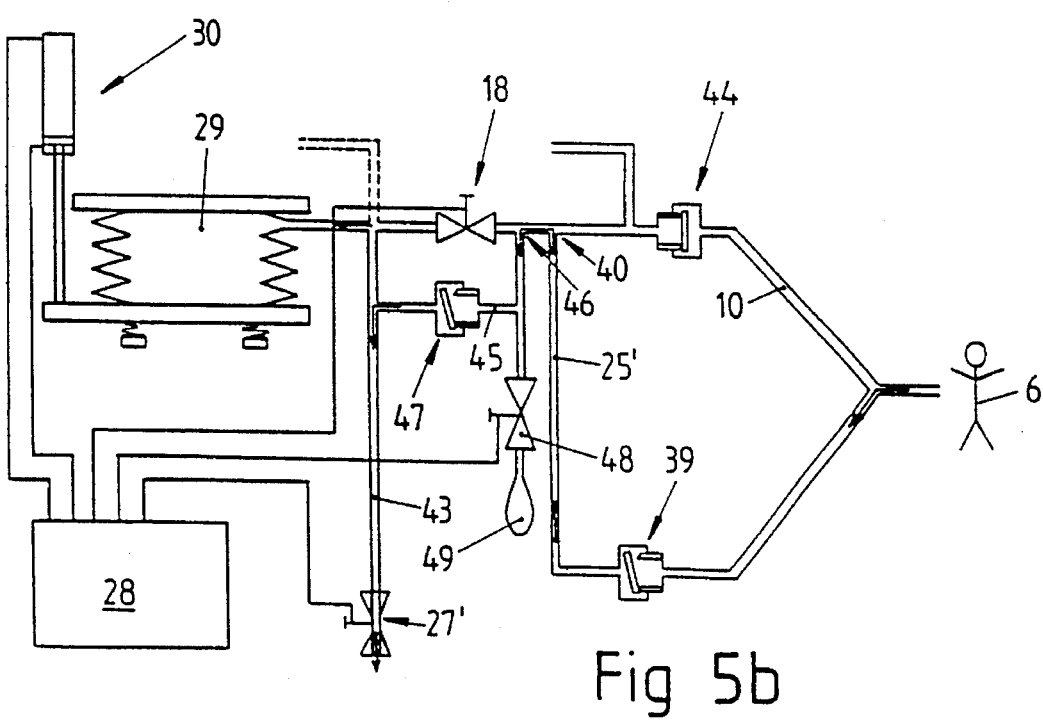
Figure 6:
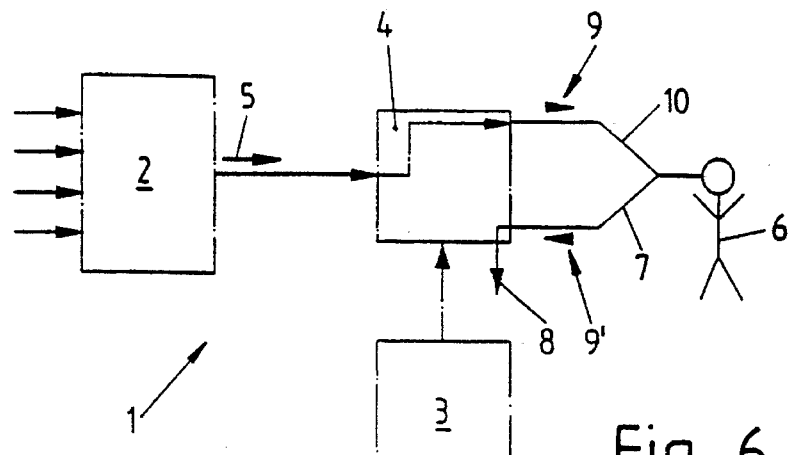
FIGS. 6–8 are schematics of known anesthetic machines.
Figure 7:
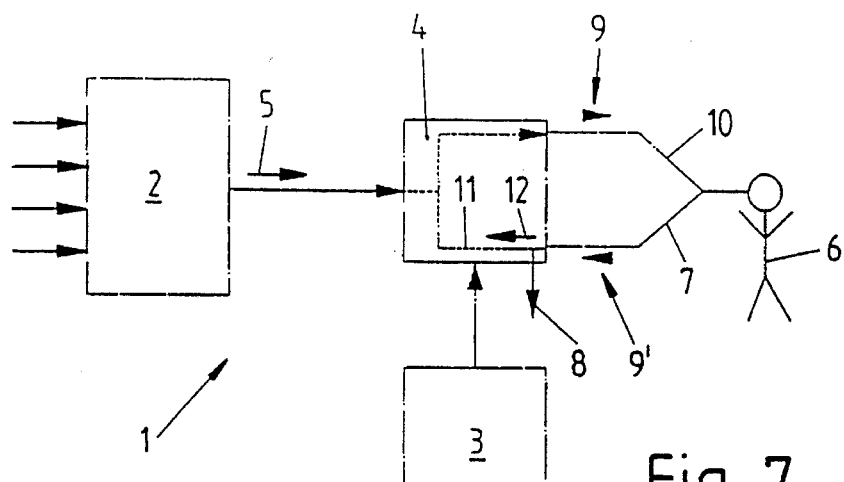

The exemplary embodiment of the invention shown in FIGS. 5a, 5b represents a simple further development of the exemplary embodiment shown in FIGS. 4a, 4b. Identical parts are provided with identical reference numbers. In the exemplary embodiment shown in FIGS. 5a, 5b it is possible for the system shown in FIG. 4, and in principle the system of FIGS. 1 to 3, to be provided with a connectable manual ventilation. For this purpose, another controllable valve 48 is connected to line 45 and leads to the inspiratory branch via the upper T piece 46. This makes it possible for manually controlled ventilation of the patient to be carried out additionally by means of a manual bellows 49 during the inspiratory phase as long as the controllable valve 48 is open.

The valve 48 can be open during the expiratory phase so that fresh gas and, where appropriate, expiratory gas can reach the manual ventilation bellows 49.

Also indicated in FIG. 1a is a measuring unit 50, which is close to the patient and is intended to pick up the spontaneous breathing activity of the patient, for the reduced pressure generated by the spontaneous breathing and/or the gas flow. This "trigger unit" controls the controllable inspiration valve 18 and generates an additional respiratory support or spontaneous breathing assistance.

The invention is not confined to the exemplary embodiments depicted and described. On the contrary, it also embraces all expert further developments within the scope of the inventive concept. In particular, the alternating pressure gas store 29 can also be designed as piston/cylinder unit with its own controllable actuation in both directions.

I claim:

1. An anesthetic machine, comprising:
   (A) a pressure generator for supporting and performing ventilation of a patient, and comprising an alternating pressure gas storage device defining a stroke volume, and controllable actuation means operatively connected to said gas storage device for increasing the stroke volume;

(B) anesthetic gas exchange means for performing a gas exchange between the anesthetic machine and a patient, comprising:
  (1) an inspiratory branch supplying an inspiratory gas to the patient, and having a first end attached to said pressure generator;
  (2) an expiratory branch receiving an expiratory gas from the patient;
  (3) a patient-connecting T-piece having a first leg connected to a second end of said inspiratory branch, a second leg connected to an end of said expiratory branch, and a third leg for supplying the inspiratory gas and receiving the expiratory gas to and from the patient;
  (4) a controllable inspiration valve located in the inspiratory branch downstream of said pressure generator for removing a gas under pressure during an inspiratory phase from said gas storage device;
  (5) an expiration valve located in the expiratory branch;
  (6) a connecting line connecting said inspiratory branch to a location on said expiratory branch downstream of said expiration valve, said connecting line receiving the expiratory gas from the patient and supplying the expiratory gas to said gas storage device; and
  (7) a controllable surplus valve in communication with said expiratory branch for controlling an amount of expiratory gas supplied to said gas storage device through said expiratory branch and said connecting line, said anesthetic machine forming one of a half-closed, closed, and half-open anesthetic system in dependence on a position of said surplus valve; and (C) anesthetic delivery means connected to said inspiratory branch for delivering fresh gas to the patient.

2. The anesthetic machine defined in claim 1, wherein the gas under pressure in said gas storage device is a respiratory gas, the pressure of the respiratory gas being controlled by said controllable inspiration valve and being reduced during an expiration phase so that the expiration gas is passed through said connecting line and collected in said gas storage device.

3. The anesthetic machine defined in claim 1, further comprising means for partially reusing the expiration gas by recirculating a portion of the expiration gas to said gas storage device, and by diverting excess expiration gas using said controllable surplus valve.

4. The anesthetic machine defined in claim 1, wherein said expiration valve comprises a PEEP valve having means for generating a continuous positive airway pressure.

5. The anesthetic machine defined in claim 1, further comprising a supply line connecting said anesthetic delivery means to a location on said inspiratory branch, said location being one of upstream and downstream of said controllable inspiration valve.

6. The anesthetic machine defined in claim 5, further comprising means for one of intermittently and continuously supplying the fresh gas through said supply line.

7. The anesthetic machine defined in claim 1, wherein said gas storage device includes a fixed plate, a movable plate, and spring means for actuating said movable plate to reduce the stroke volume.

8. The anesthetic machine defined in claim 1, wherein said controllable actuation means comprises a piston and cylinder unit, said piston and cylinder unit being one of pneumatically and electrically actuated.

9. The anesthetic machine defined in claim 1, wherein said connecting line includes a non-return valve located therein, said non-return valve being closed during the inspiratory phase.

10. The anesthetic machine defined in claim 1, wherein said controllable surplus valve and said expiration valve are located in said expiratory branch; said expiration valve being controllable; and said connecting line branching off from said expiratory branch at a location between said controllable surplus valve and said expiration valve.

11. The anesthetic machine defined in claim 1, wherein said expiration valve comprises a non-return valve, said non-return valve closing said expiratory branch relative to said inspiratory branch; and wherein said surplus valve comprises a combined surplus, expiration and PEEP valve.

12. The anesthetic machine defined in claim 1, wherein said connecting line returns a respiratory gas to said inspiratory branch and to said gas storage device; and wherein said surplus valve comprises a combined surplus, expiration and PEEP valve connected to said inspiratory branch.

13. The anesthetic machine defined in claim 12, wherein said connecting line opens into said inspiratory branch at a location between the patient and said controllable inspiration valve; wherein said anesthetic gas exchange means further comprises a bypass line having a non-return valve, said bypass line bridging said controllable inspiration valve, said non-return valve being closed during the inspiratory phase.

14. The anesthetic machine defined in claim 1, further comprising a manual ventilation unit having a control valve connected to said inspiratory branch.

15. The anesthetic machine defined in claim 1, further comprising a trigger means for registering a breathing of the patient and controlling said inspiration valve; wherein said gas storage device is operatively connected to said inspiration valve and said trigger means for supplying the inspiratory gas to a spontaneously breathing patient.

16. The anesthetic machine defined in claim 15, wherein said trigger means provides the spontaneously breathing patient with inspiratory respiratory support.

* * * * *